United States Patent
Lowery et al.

(10) Patent No.: US 11,854,363 B2
(45) Date of Patent: Dec. 26, 2023

(54) LIGHT SENSOR AMBLYOPIA PATCH DEVICE

(71) Applicants: Robert S. Lowery, Little Rock, AR (US); Michael D. Kaczkowski, Jacksonville, AR (US); Zigmond Robert Gustafson, North Little Rock, AR (US)

(72) Inventors: Robert S. Lowery, Little Rock, AR (US); Michael D. Kaczkowski, Jacksonville, AR (US); Zigmond Robert Gustafson, North Little Rock, AR (US)

(73) Assignees: BioVentures, LLC, Little Rock, AR (US); Arkansas Children's Research Institute, Little Rock, AR (US)

( * ) Notice: Subject to any disclaimer, the term of this patent is extended or adjusted under 35 U.S.C. 154(b) by 0 days.

(21) Appl. No.: 17/668,703

(22) Filed: Feb. 10, 2022

(65) Prior Publication Data
US 2022/0254238 A1    Aug. 11, 2022

Related U.S. Application Data

(60) Provisional application No. 63/147,917, filed on Feb. 10, 2021.

(51) Int. Cl.
*G08B 21/02* (2006.01)
*G08B 21/18* (2006.01)
*A61F 9/04* (2006.01)

(52) U.S. Cl.
CPC .............. *G08B 21/02* (2013.01); *A61F 9/045* (2013.01); *G08B 21/182* (2013.01)

(58) Field of Classification Search
CPC ........ G08B 21/02; G08B 21/182; A61F 9/045
USPC .......................................... 340/600
See application file for complete search history.

(56) References Cited

U.S. PATENT DOCUMENTS

| | | | |
|---|---|---|---|
| 6,786,601 B1 * | 9/2004 | Kurup .................. | A61F 9/04 2/15 |
| 9,032,962 B2 * | 5/2015 | Van Dalen ............ | A61F 9/04 351/203 |
| 2012/0123313 A1 * | 5/2012 | Van Dalen ............ | A61F 9/04 602/61 |
| 2012/0209355 A1 * | 8/2012 | Witt .................... | A61M 21/02 607/88 |
| 2012/0212706 A1 * | 8/2012 | Chou .................. | A61B 3/036 351/246 |
| 2013/0060306 A1 * | 3/2013 | Colbauch ............ | A61N 5/0618 607/88 |
| 2016/0026009 A1 * | 1/2016 | Urbajs ................ | G02C 7/101 349/13 |

(Continued)

OTHER PUBLICATIONS

Friedman, et al., Prevalence of Amblyopia and Strabismus in White and African-American Children Aged 6 Through 71 Months: The Baltimore Pediatric Eye Disease Study, Ophthalmology, Nov. 2009, 116(11): 2128-34.

*Primary Examiner* — Zhen Y Wu
(74) *Attorney, Agent, or Firm* — Richard Blakely Glasgow (57) ABSTRACT

An amblyopia patch device including an eye patch, a light sensor attached to the eye patch, an alarm in communication with the light sensor, and an electronics system for triggering the alarm when the light sensor senses a light value above a pre-set threshold. A method of using the amblyopia patch device is also disclosed.

18 Claims, 6 Drawing Sheets

(56) References Cited

U.S. PATENT DOCUMENTS

| | | | |
|---|---|---|---|
| 2016/0256050 A1* | 9/2016 | Geertsen | A61B 3/145 |
| 2019/0290528 A1* | 9/2019 | Sgambelluri | A61H 5/00 |
| 2019/0343452 A1* | 11/2019 | Ellspermann | A61B 5/7405 |
| 2020/0306493 A1* | 10/2020 | Lee | A61B 5/165 |
| 2021/0208425 A1* | 7/2021 | Petrillo, Sr. | A61F 9/023 |
| 2021/0353219 A1* | 11/2021 | Narayanan | A61B 5/4809 |
| 2022/0137435 A1* | 5/2022 | Spiegel | G02C 11/10 |
| | | | 351/158 |

* cited by examiner

LIGHT SENSOR AMBLYOPIA PATCH DEVICE

CROSS-REFERENCE TO RELATED APPLICATIONS

This application claims the benefit of U.S. Provisional Application No. 63/147,917, entitled "Light Sensor Amblyopia Patch Device" and filed on Feb. 10, 2021. The complete disclosure of said patent application is hereby incorporated by reference.

STATEMENT REGARDING FEDERALLY SPONSORED RESEARCH OR DEVELOPMENT

Not applicable

BACKGROUND OF THE INVENTION

Amblyopia (commonly called "lazy eye") is a vision development disorder. In children with this disorder, the brain over time relies more and more on the stronger eye and the vision in the lazy eye can be permanently poor without reversal of this condition by a certain age. Children with amblyopia are often treated by patching the stronger eye, which forces the child to use and strengthen the lazy eye. However, children often do very poorly with conventional patching because they cheat by pulling the patch off completely or adjust it in order to see around the patch without their parents noticing. As a result, it is difficult to determine the actual amount of time that proper patching is being done. It would therefore be desirable to develop an eye patch that senses when the stronger eye is not covered and alerts the parents.

BRIEF SUMMARY OF THE INVENTION

The present invention is directed to an amblyopia patch device that includes an eye patch, a light sensor attached to the eye patch, an alarm in communication with the light sensor, and an electronics system configured to trigger the alarm when the light sensor senses a light value above a pre-set threshold. In addition, the present invention is directed to an amblyopia patch device that includes an eye patch, a light sensor attached to the eye patch, and an electronics system in communication with a smart device. The electronics system is configured to trigger a notification on the smart device when the light sensor senses a light value above a pre-set threshold. The present invention is also directed to a method of using the amblyopia patch device comprising the steps of attaching the amblyopia patch device to the head of a patient with amblyopia, covering an eye of the patient with the eye patch, activating the light sensor, communicating the light values sensed by the light sensor to a microcontroller of the electronic system, and triggering the alarm on the eye patch or a notification on the smart device when the light value exceeds a pre-set threshold.

These and other features, objects and advantages of the present invention will become better understood from a consideration of the following detailed description of the preferred embodiments in conjunction with the drawings as described following:

BRIEF DESCRIPTION OF THE DRAWINGS

FIG. 5A shows the microcontroller serial port assignment (top left), light sensor (top right), microcontroller (middle), and serial and programming header (bottom). FIG. 5B shows the 3.3V regulator (top), I2C resistor (middle), and alarm (bottom).

DETAILED DESCRIPTION OF THE INVENTION

With reference to FIGS. 1-7, the preferred embodiments of the present invention may be described. The amblyopia patch device 10 of the present invention includes an eye patch 12, a light sensor 14, an alarm 32, and an electronics system 28 communicating between the light sensor 14 and the alarm 32. The eye patch 12 preferably is of the type well-known to those skilled in the art. The eye patch 12 preferably completely blocks all of the light when positioned over the eye of the patient with amblyopia. The eye patch 12 may include a strap 30 for attaching the eye patch to the head of the patient. In one embodiment, as shown in FIGS. 1-4, a light seal 16 is attached to the outer surface 20 of the eye patch to ensure a tight fit over the patient's eye. For example, the light seal may be a silicone material which substantially restricts the passage of light through it. In another embodiment, the light seal 16 is omitted and the eye patch 12 alone is sized and shaped to fit tightly over the patient's eye without the need of the light seal. The eye patch 12 (with or without the light seal 16) preferably is light weight for comfort to the patient and low profile to allow glasses to fit normally on the patient's face with the eye patch 12 under the glasses. In one embodiment, the eye patch 12 includes adhesive around its perimeter to ensure a tight fit around the patient's eye. The patch device 10 may be a universal size to order to fit a wide range of patients or it may be made in a variety of sizes.

Figure 4:
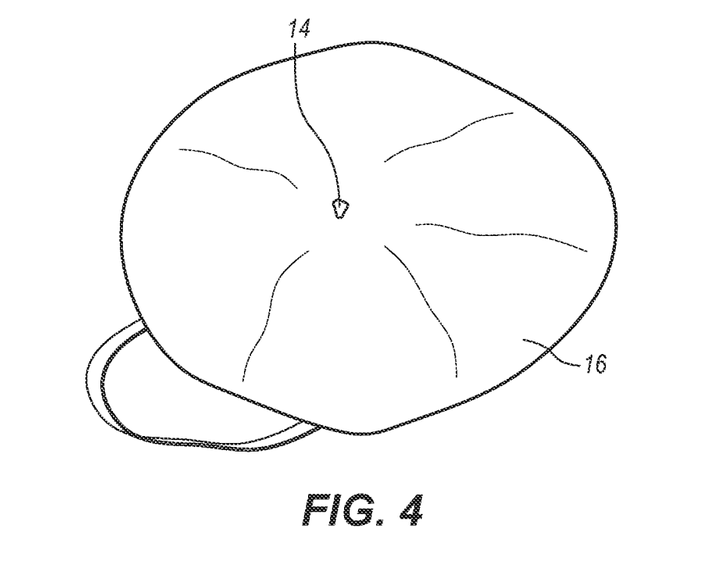
FIG. 4 is a front perspective view of a preferred embodiment of the patch device.

The light sensor 14 is attached to the inside surface 18 of the eye patch. If a light seal 16 is included, the light sensor 14 preferably is aligned with an opening in the light seal 16, as shown in FIG. 4. In one embodiment, the light sensor 14 is glued to the eye patch 12. The light sensor 14 preferably is of the type well-known to those skilled in the art. For example, in one embodiment, the light sensor 14 is an AMS TSL2591 high dynamic range digital light sensor. The TSL2591 light sensor is a very high sensitivity light-to-digital converter that transforms light intensity into a digital signal output capable of direct I2C interface. This light sensor is preferable due to its the very high dynamic range and low light sensitivity. Other sensors were evaluated by the inventors, but the light level change between the patch worn correctly and partially removed was not easily discernible from noise. The light sensor can be configured for better performance at low light levels and gives usable readings to determine if the eye is covered completely. In addition, the sensor is designed for low power applications and incorporates all the analog measurement circuitry in a very small package.

Figures 1, 2:
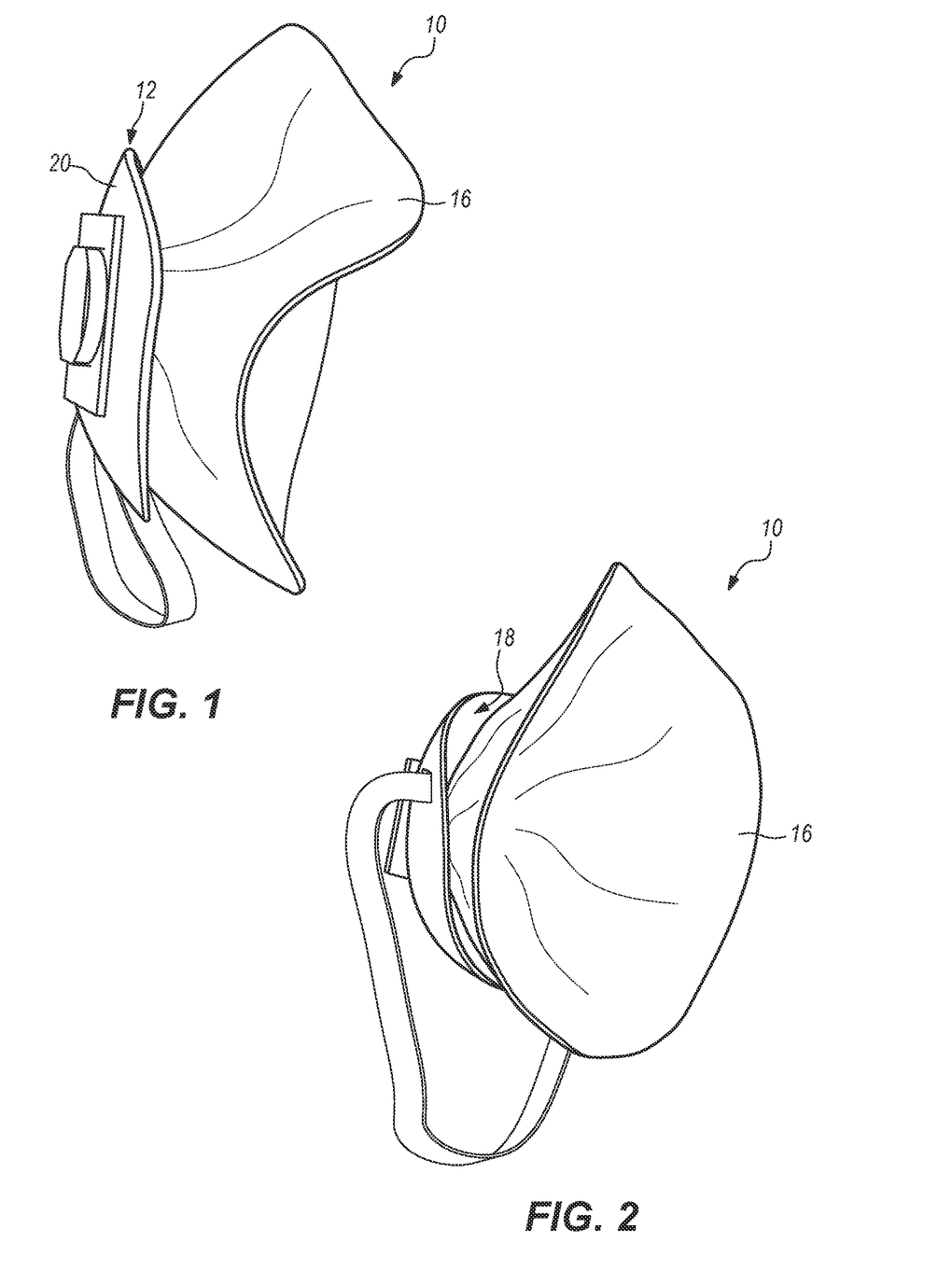
FIG. 1 is a side perspective view of a preferred embodiment of the amblyopia patch device.
FIG. 2 is a front perspective view of a preferred embodiment of the amblyopia patch device.
Figure 3:
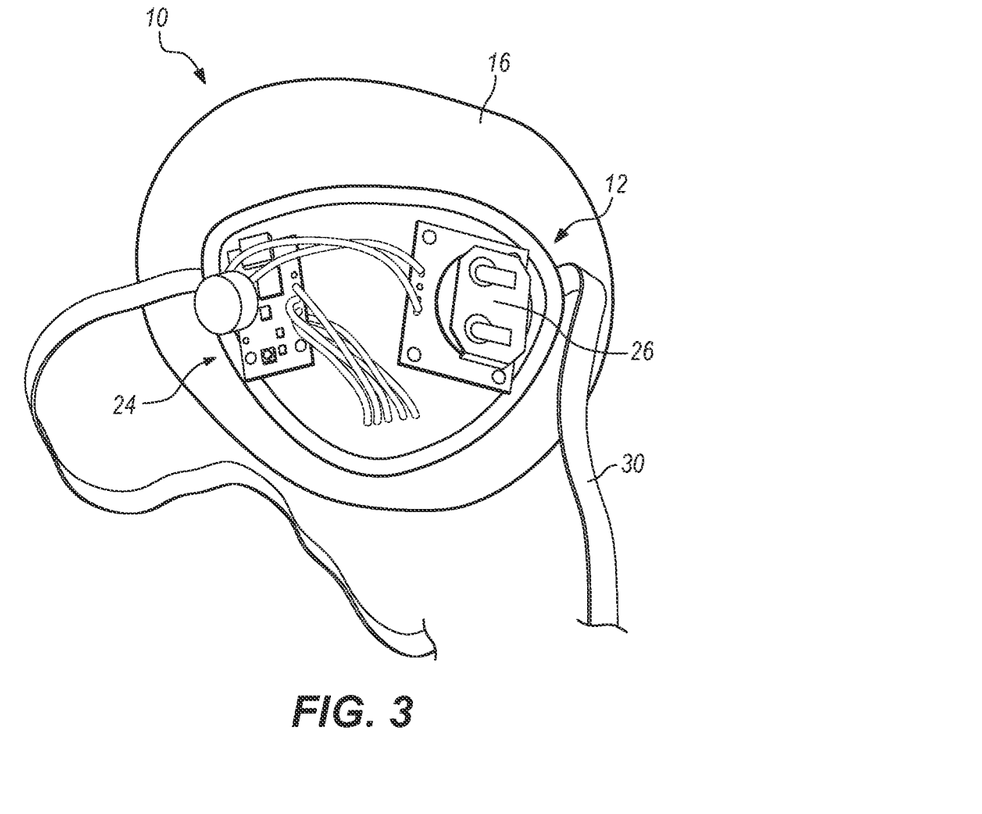
FIG. 3 is a back perspective view of a preferred embodiment of the amblyopia patch device.

As shown in FIG. 3, a microcontroller 24 is attached to outer surface 20 of the eye patch 12. In one embodiment, the microcontroller 24 is glued to the eye patch 12. The microcontroller 24 is preferably of the type well-known to those skilled in the art. For example, in one embodiment, the microcontroller 24 is a SAMD21 microcontroller. This microcontroller was selected due to its small and lightweight board (the Adafruit Trinket M0) and the operating voltage being compatible with a 3V Lithium coin cell battery. A battery 26 is also attached to the outer surface of the eye patch 12. The battery is preferably of the type well-known to those skilled in the art. For example, in one embodiment, the battery 26 is a 3V Lithium coin cell battery. This battery is easily replaceable, provides consistent power without additional components, and is very low weight.

Figure 5A:
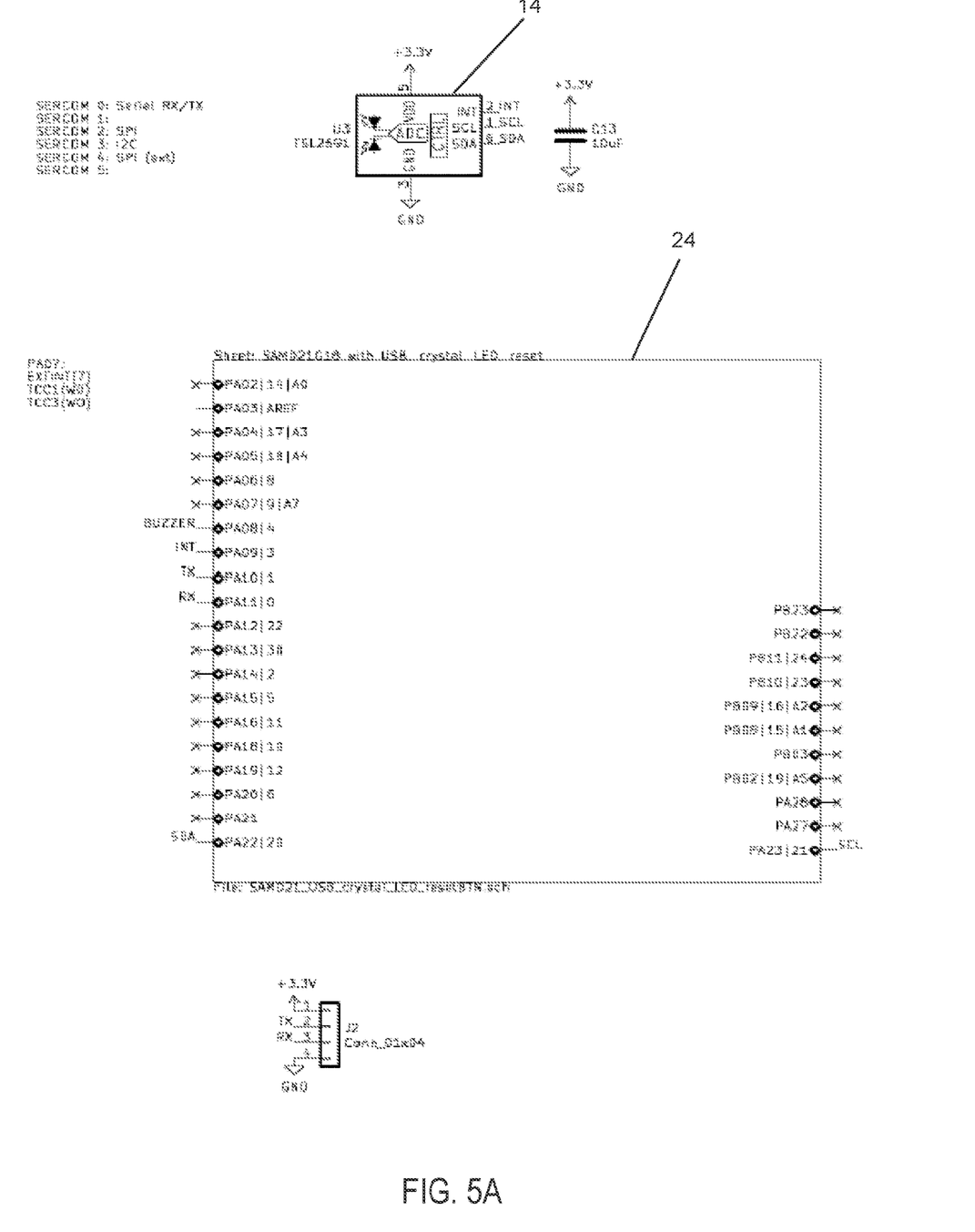
FIGS. 5A-5B are schematics of the electronics system of a preferred embodiment of the amblyopia patch device.
Figure 5B:
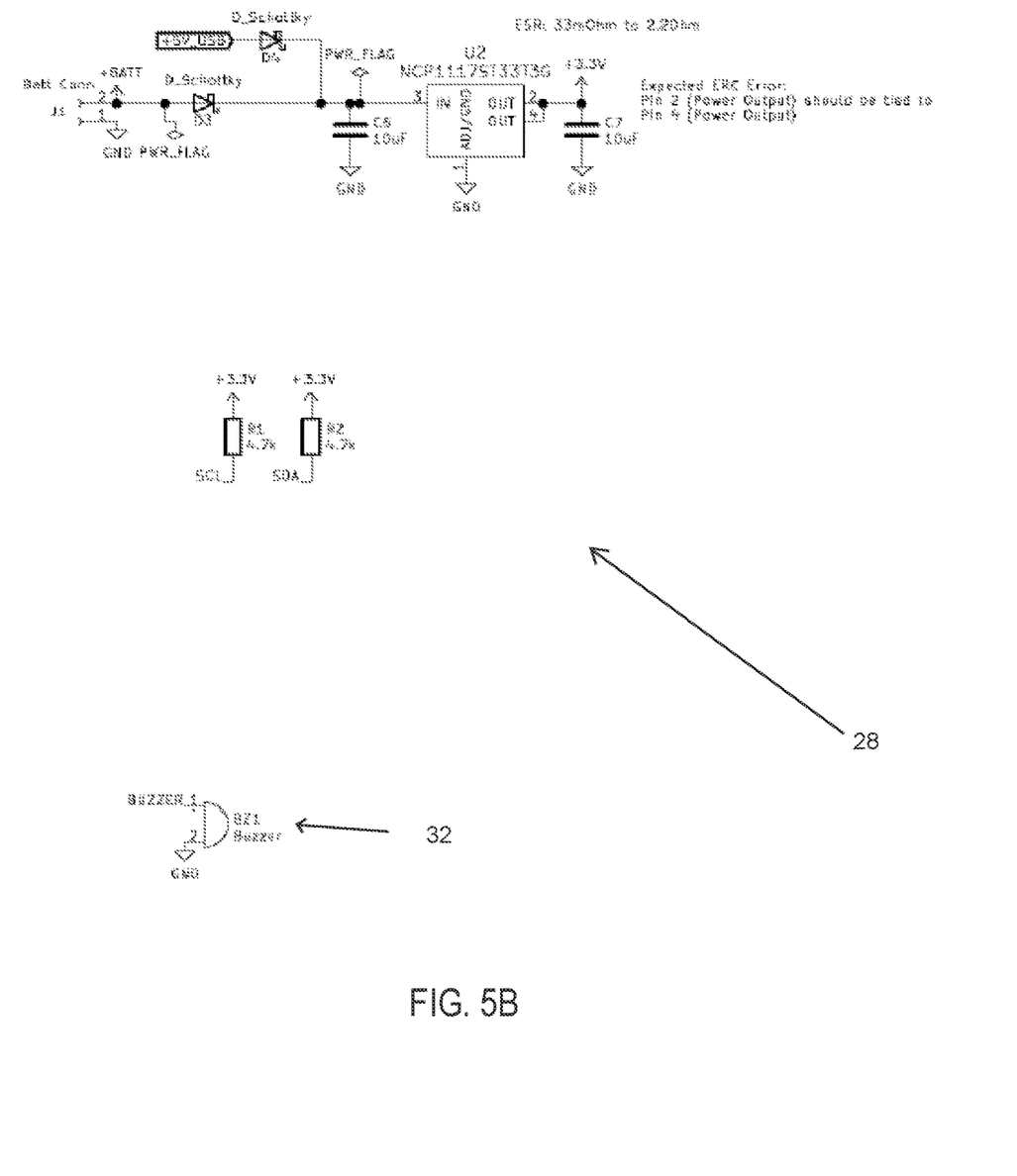
Figure 6:
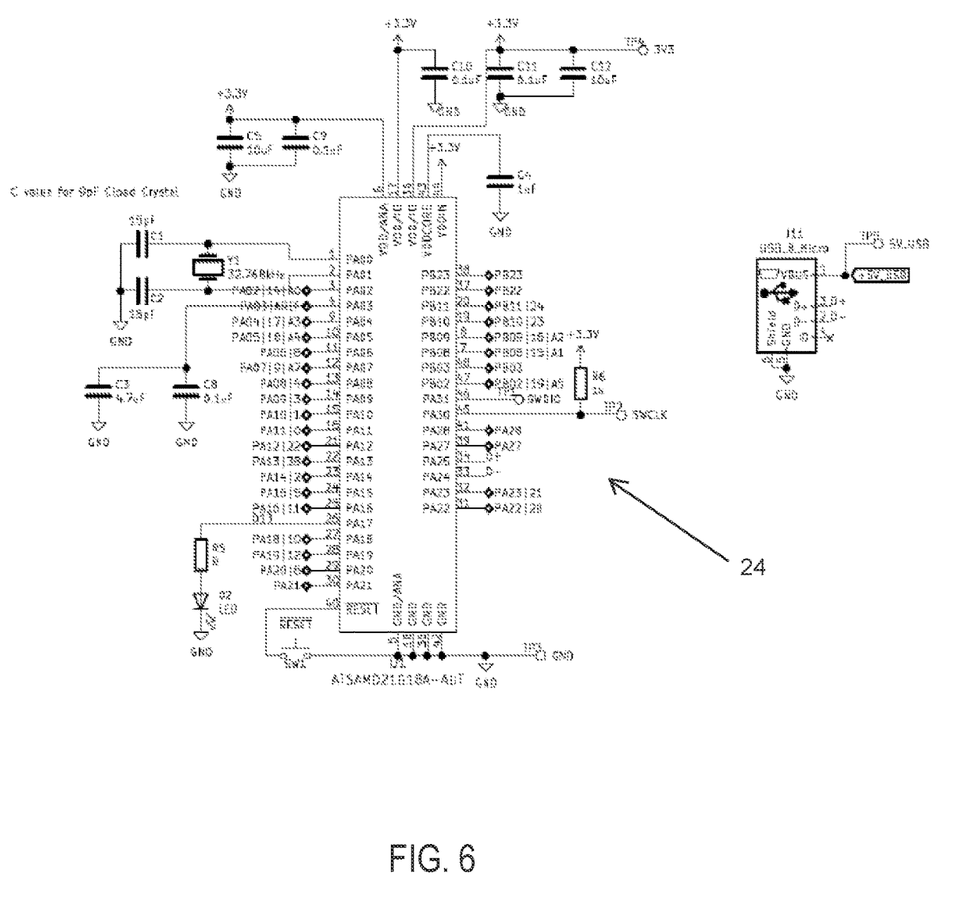
FIG. 6 is an electrical schematic for the microcontroller of a preferred embodiment of the amblyopia patch device.

Electrical schematics for the amblyopia patch device are shown in FIGS. 5A-6. The microcontroller 24 and the light sensor 14 are both powered directly from the battery 26. The light sensor 14 is connected to, and communicates with, the microcontroller 24 via a bus, such as an I2C bus. The microcontroller 24 is connected to, and communicates with, an alarm 32 (e.g., small piezo buzzer) and a LED light for user interaction. The LED light indicates when the device 10 is turned on and being powered by the battery. The microcontroller 24 also includes a reset button to restart the microcontroller.

On startup, the microcontroller 24 begins requesting ambient light values from the light sensor 14 every few seconds. The light sensor 14 and the microcontroller 24 operate in low power states between readings to conserve the battery 26. Once the light values drop below a first pre-set threshold that indicates that the patch has been placed over an eye, the microcontroller requests light values several times per second. If the light value is greater than a second pre-set threshold (also referred to as the alarm threshold), the patch is put into an alarm state that indicates that it needs to be adjusted or it has been removed. The alarm may be reset by adjusting the patch to reduce the light reading or by pressing the reset button on the patch if the patch is being removed. While the patch device 10 is being worn, the alarm threshold is automatically adjusted based on the most recent ambient light levels. This helps to adjust for changes in external light levels, such as moving between rooms. In another embodiment, the patient or the patient's caregiver is able to manually adjust the light sensitivity of the sensor for different lighting conditions.

The electronic system 28 of the patch device 10 also preferably includes wireless technology, such as Bluetooth® wireless technology, to connect the patch device 10 to a smart device, such as a smartphone. In one embodiment, the microcontroller 24 communicates with the smart device. The electronic system includes a timer that tracks the amount of time the patch device 10 is being used in the alarm and non-alarm state. That data is accessible on a mobile application that is downloadable to the smart device. The electronic system is also capable of recording other usage metrics of the patch device that are accessible on the app, such as the number of times the patch device is removed. This information is also reportable to the physician's office through the app.

Figure 7:
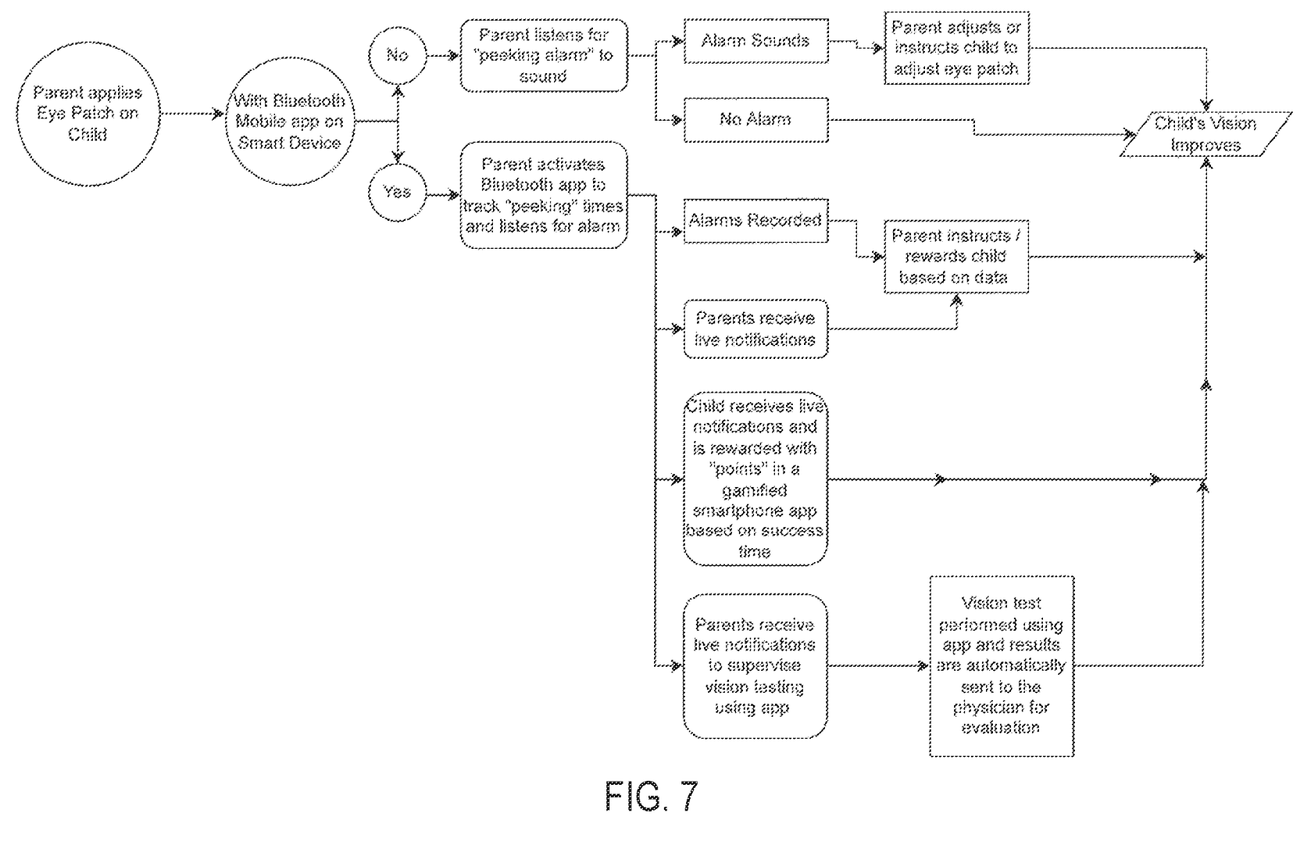
FIG. 7 is a logic flowchart for the operation of the amblyopia patch device.

FIG. 7 shows a logic flowchart for use of the amblyopia patch device of the present invention. A parent applies the patch device 10 over the child's eye and turns on the device. If there is no alarm, then the patch device is positioned properly. If an alarm sounds, the parent adjusts the patch device such that the amount of light received by the light sensor does not exceed the pre-set alarm threshold. Alternatively, the parent may instruct the child to adjust the patch device. Once the patch device is properly positioned, the child plays with the patch device covering his or her eye for a pre-set amount of time. If the alarm sounds during that pre-set time, the parents or the child adjusts the patch until the amount of light received by the light sensor does not exceed the pre-set alarm threshold and thus the alarm is no longer sounding. After the pre-set amount of time has passed, the patch device is removed from the child's eye.

In one embodiment, instead of listening for the audible alarm 32 on the patch device 10, the parent receives live notifications, including audible notifications, from the app when the patch device is in the alarm state. The electronics system 28 is in communication with the smart device, and the electronics system 28 triggers a notification on the smart device through the app when the light sensor senses a light value above a pre-set threshold. Text and email messages may also be sent to the parent. In one embodiment, the child receives points in the app based on the child's performance wearing the patch device. The child may be rewarded through the app with games being unlocked after certain point thresholds are met.

The app on the smart device that is in communication with the patch device 10 includes a vision acuity test. The app displays the letters or images for the test on the screen, and the camera of the smart device determines the distance of the screen from the patient's face. During the test, the patient responds to audible questions and the answers from the patient are provided in real time. If the smart device is moved closer to the patient's face than acceptable for that particular test, an error will be triggered through the app and the test data will be invalidated. The patient will then start a new test. The results of the vision acuity test can then be reported to the eye doctor's office. Because the eye doctor can track the changes in the patient's vision through the app, the patient is saved visits to the eye clinic. The invention therefore is beneficial for telemedicine.

The present invention has been described with reference to certain preferred and alternative embodiments that are intended to be exemplary only and not limiting to the full scope of the present invention.

We claim:

1. An amblyopia patch device comprising:
 an eye patch having an inner surface and an outer surface;
 a light sensor attached to said inner surface of said eye patch, wherein said inner surface of said eye patch is configured to face an eye of a patient when said eye patch covers said eye;
 an alarm in communication with said light sensor; and
 an electronics system configured to trigger said alarm when said light sensor senses a light value above a pre-set threshold.

2. The amblyopia patch device of claim 1, further comprising a light seal attached to said eye patch.

3. The amblyopia patch device of claim 1, wherein said eye patch comprises an adhesive around the perimeter of said eye patch.

4. The amblyopia patch device of claim 2, wherein said light seal comprises an opening.

5. The amblyopia patch device of claim 4, wherein said light sensor is aligned with said opening in said light seal.

6. The amblyopia patch device of claim 1, wherein said electronics system comprises a microcontroller.

7. The amblyopia patch device of claim 6, wherein said light sensor and said microcontroller are powered by a battery.

8. The amblyopia patch device of claim 6, wherein said microcontroller is configured to communicate with said light sensor.

9. The amblyopia patch device of claim 6, wherein said microcontroller is configured to communicate with said alarm.

10. The amblyopia patch device of claim 1, wherein said amblyopia patch device is connectable to a smart device.

11. The amblyopia patch device of claim 1, wherein said eye patch comprises a strap for attaching said eye patch to said patient's head.

12. The amblyopia patch device of claim 1, further comprising a light emitting diode (LED) light for indicating when said amblyopia patch device is powered.

13. The amblyopia patch device of claim 7, wherein said microcontroller and said battery are attached to said outer surface of said eye patch.

14. The amblyopia patch device of claim 10, wherein said smart device comprises a mobile application, wherein said mobile application is operable to track usage of said patch device and report said usage of said patch device to a medical provider.

15. An amblyopia patch device comprising:
   an eye patch having an inner surface and an outer surface;
   a light sensor attached to said inner surface of said eye patch, wherein said inner surface of said eye patch is configured to face an eye of a patient when said eye patch covers said eye; and
   an electronics system in communication with a smart device, wherein said electronics system is configured to trigger a notification on said smart device when said light sensor senses a light value above a pre-set threshold.

16. The amblyopia patch device of claim 15, wherein said smart device comprises a mobile application, wherein a vision acuity test is accessible in said mobile application, wherein said mobile application is operable to report a result of said vision acuity test to a medical provider.

17. A method of using an amblyopia patch device, wherein said method comprises the steps of:
   attaching an amblyopia patch device to a head of a patient with amblyopia, wherein said amblyopia patch device comprises an eye patch and a light sensor connected to an inner surface of said eye patch;
   covering an eye of said patient with said eye patch, wherein said inner surface of said eye patch faces said eye of said patient;
   activating said light sensor;
   communicating a light value sensed by said light sensor to a microcontroller; and
   triggering an alarm on said eye patch or a notification on a smart device when said light value exceeds a pre-set threshold.

18. The method of using an amblyopia patch device of claim 16, further comprising the step of removing said amblyopia patch device from said head of said patient after a pre-set amount of time.

\* \* \* \* \*